United States Patent [19]

McCarthy, deceased et al.

[11] Patent Number: 5,019,390
[45] Date of Patent: May 28, 1991

[54] ANTICANCER AGENT—IMIC

[75] Inventors: Robert D. McCarthy, deceased, late of RD Aaronsburg, by Jeanne L. McCarthy, administratrix; Arun Kilara; David B. Pierce, both of State College, all of Pa.

[73] Assignee: Research Corporation Technologies, Inc., Tucson, Ariz.

[21] Appl. No.: 56,504

[22] Filed: May 29, 1987

[51] Int. Cl.$^5$ .............................................. H61K 35/12
[52] U.S. Cl. .................................................. 424/535
[58] Field of Search .............................. 514/2; 424/95

[56] References Cited

U.S. PATENT DOCUMENTS 4,427,658  1/1984  Maubois et al. ...................... 514/2

*Primary Examiner*—Delbert R. Phillips
*Attorney, Agent, or Firm*—Scully, Scott, Murphy & Presser

[57] ABSTRACT

The present invention relates to a novel antineoplastic agent, designated IMIC (Inhibitor of Mevalonate Incorporation Into Cholesterol) having the following characteristics:

(a) is present in the retentate of dialyzed skim milk;
(b) is non-dialyzable;
(c) has general properties of pyrimidines;
(d) is bound to a protein in the proteose-peptone fration of milk;
(e) is soluble in water;
(f) is insoluble in organic solvents;
(g) is stable in acid;
(h) is not bound or retained by a $C_{18}$ or $C_8$ reverse phase HPLC columns;
(i) is not retained by a $C_{18}$ or silica gel sep. pak;
(j) has λ maximum absorbance at 208 nm and 278 nm (UV) in neutral ad acidic solution and in a basic solution at 223 and 290 nm;
(k) provides peaks with a retention time of 7.52 minutes upon fractionation by HFLC on a Biorad Aminex resin column (30 cm ×7.9 nm) with 0.05 $NH_2SO_4$ as the mobile phase and with a flow rate of 0.7 ml/minute;
(l) provides peaks with a retention time of 9.9 minutes upon fractionation on an HPLC Biorad Ag 50 Mx-8 resin column (22 mm×20 cm) with 0.035N formic acid as the mobil phase and a flow rate of 4 ml/minutes.
(m) inhibits cholesterolgenesis by inhibiting mevalonate incorporation into cholesterol along the cholesterol biosynthetic pathway.

IMIC can be employed in compositions of pharmaceutically acceptable. dosages and, specifically, in a method of treating neoplastic disorders in mammals.

17 Claims, 6 Drawing Sheets

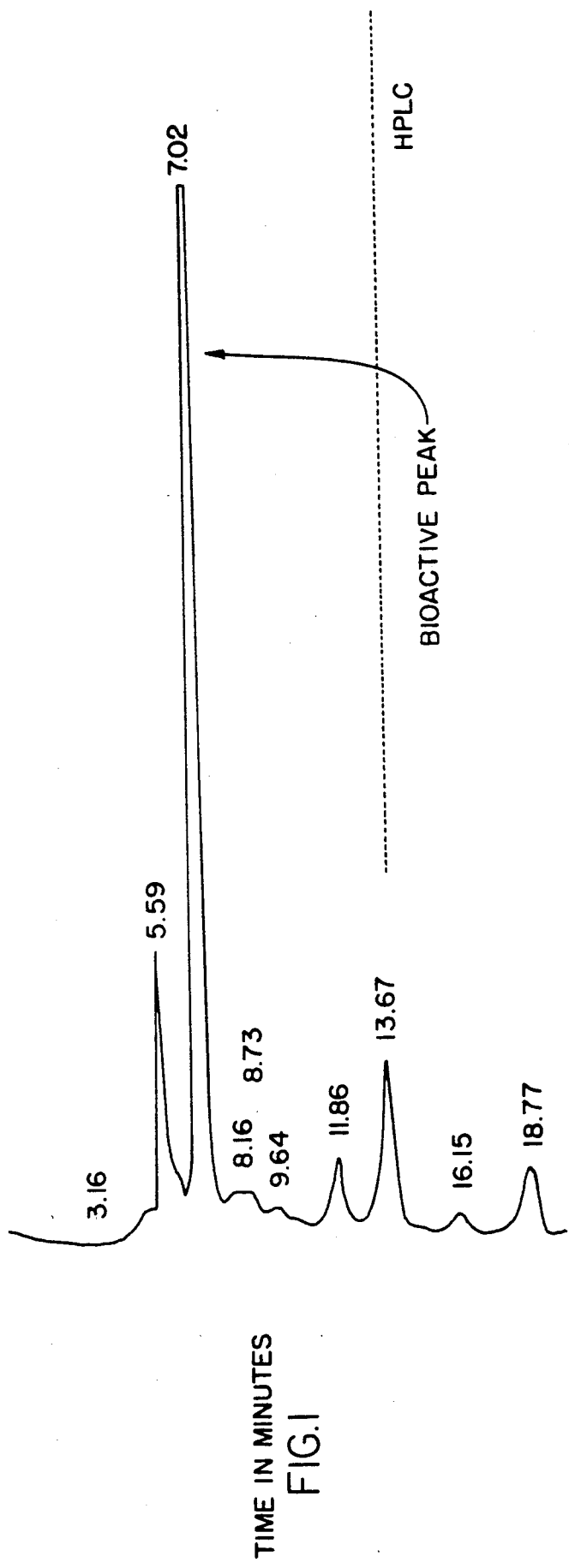

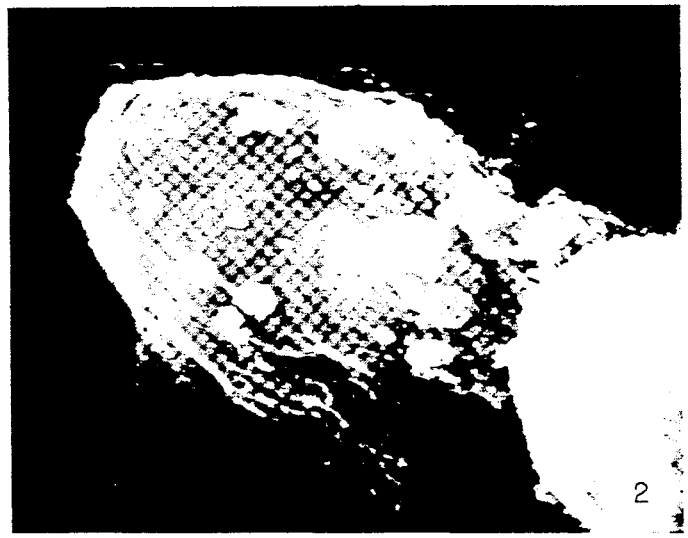
FIG. 2 SCANNING ELECTRON MICROGRAPH OF P388 LEUKEMIA CONTROL CELLS 5,000X.
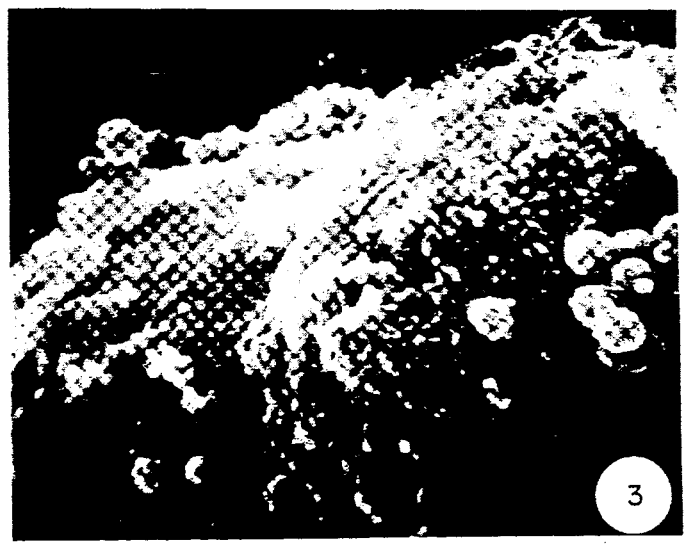
FIG. 3 SCANNING ELECTRON MICROGRAPH OF P388 LEUKEMIA CONTROL CELLS 10,000X.
NOTE: FILIPODIA AND NUMEROUS BLEBS.

FIG. 4 SCANNING ELECTRON MICROGRAPH OF P388 LEUKEMIA CELLS TREATED WITH IMIC FOR 48 HOURS AT 37°C. 5,000X.
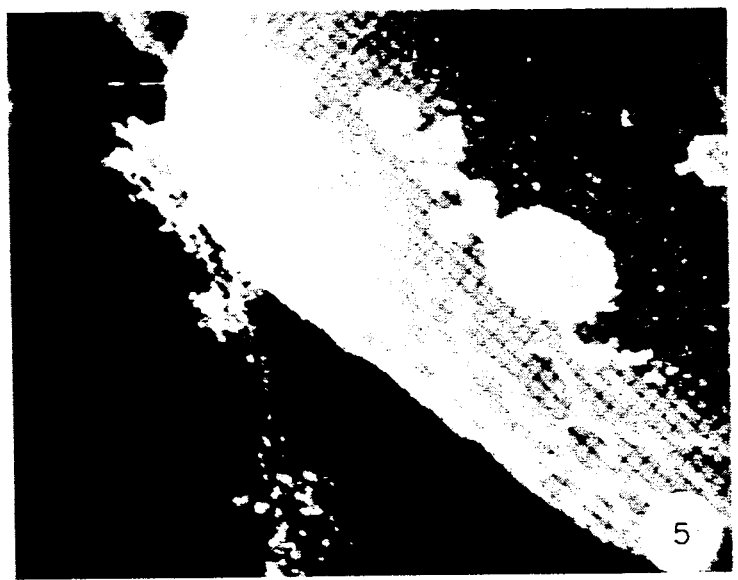
FIG. 5 SCANNING ELECTRON MICROGRAPH OF P388 LEUKEMIA CELLS TREATED WITH IMIC FOR 48 HOURS AT 37°C. 10,000X.
NOTE: POLYSACCHRIDE STRINGS, FEWER BLEBS AND MEMBRANE INDENTATIONS; ALL INDICATING DYING CELLS.

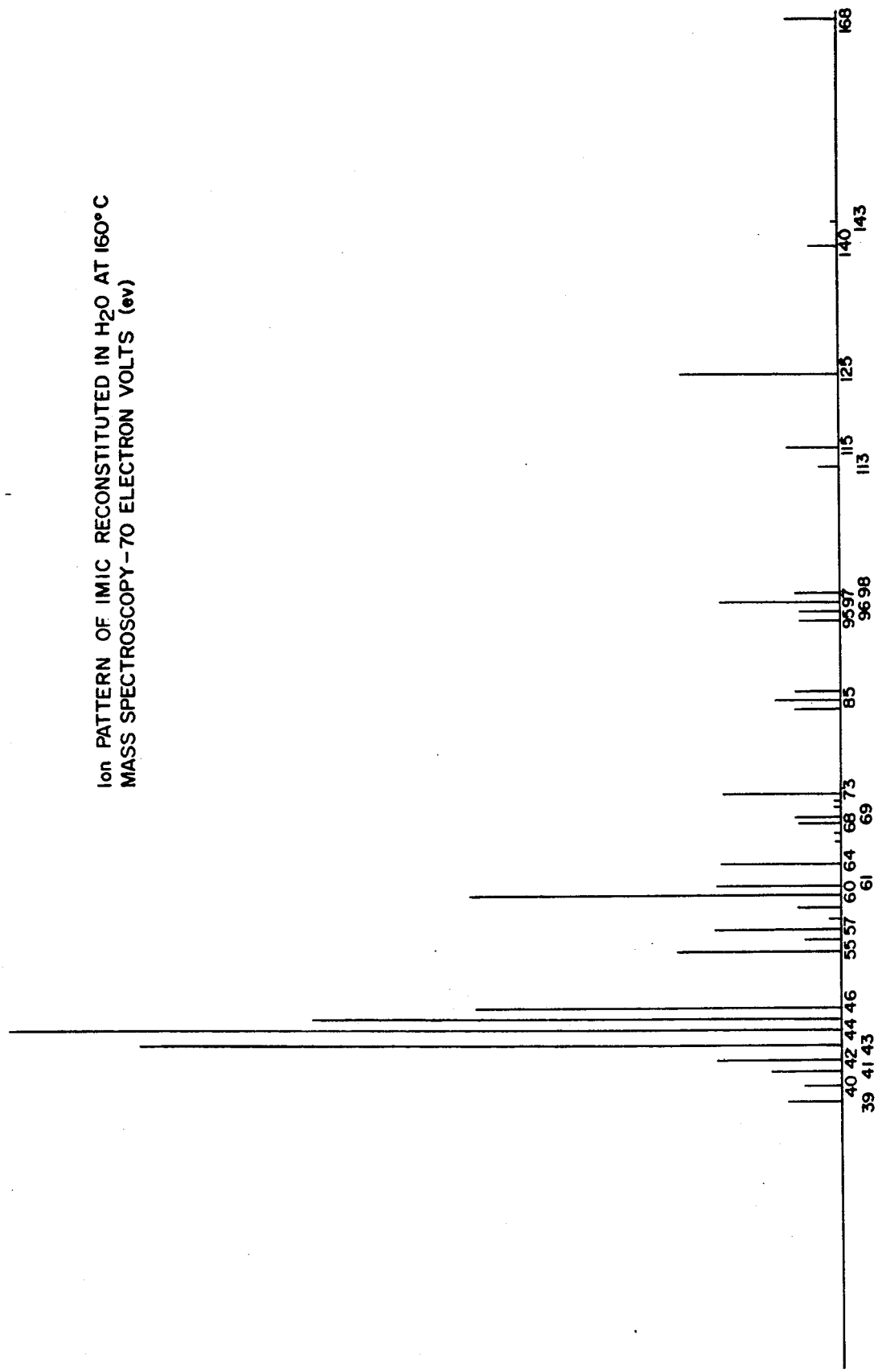

COULTIER MACDS CELL FLOW CYTOMETER--CELL POPULATION ANALYSIS IN VITRO LEUKEMIA CELLS--CONTROL SAMPLE--48 HOUR INCUBATION CELLS STAINED WITH HOECHST 33342 DNA SPECIFIC FLUOROCHROME FOR LIVING CELLS THE DENSITY OF THE DOTS ARE PROPORTIONAL TO THE NUMBERS OF LIVE CELLS

COULTIER MACDS CELL FLOW CYTOMETER--CELL POPULATION ANALYSIS.
IN VITRO LEUKEMIA CELLS--IMIC TREATMENT--48 HOUR INCUBATION.
CELLS STAINED WITH HOECHST 33342 DNA SPECIFIC FLUOROCHROME FOR LIVING CELLS.
THE DENSITY OF THE DOTS ARE PROPORTIONAL TO THE NUMBER OF LIVE CELLS.

ANTICANCER AGENT—IMIC

FIELD OF THE INVENTION

The present invention relates to an antineoplastic agent and a method of treating neoplastic disease. More specifically, the present invention is directed to IMIC, an isolate of skim milk which inhibits mevalonate incorporation into cholesterol along the cholesterol biosynthetic pathway and suppresses the formation of cholesterol, and is useful in the treatment of neoplastic diseases.

BACKGROUND OF THE INVENTION

Cholesterol is an essential component of animal cell membranes. As a structural component it is involved in maintaining the integrity of cells. By regulating the precise fluidity of cellular membranes cholesterol plays a role in the control of many cellular functions.

Cells are capable of deriving necessary cholesterol from either de novo synthesis or an external source. For hepatic cells the external source may be dietary cholesterol transported via chylomicron remnants. For extrahepatic cells the external source is low density lipoproteins (LDL). LDL are formed in the circulating blood from interactions and exchanges between liver produced very low density lipoproteins and high density lipoproteins. The cholesterol associated with LDL could have originally come from either hepatic synthesis or dietary cholesterol. Normally, a healthy cell supplied with pre-formed cholesterol, regardless of the original source, initiates a feedback mechanism which inhibits de novo synthesis of cholesterol in that cell.

Increased cholesterol content of the tumor cell's membranes results in physical changes and modifications of the functional activities of the membranes. These alterations are advantageous for cell proliferation.

Cancer cells assume a strategy which provides them with a selective growth advantage. One biochemical alteration which occurs shortly after the initiation of the cancer state is that the initiated cells devise a means for protecting de novo cholesterol synthesis from any normal regulatory mechanisms. Cancer cells accomplish this by modifying the active site of HMGCoA reductase, the primary cholesterol rate-limiting enzyme.

Overall in vivo and in vitro studies show that cancer cells lack feedback control of de novo cholesterol synthesis.

Regardless of the reasons, de novo cholesterol synthesis appears to be a prerequisite for tumor cell growth. HMGCoA reductase activity is about ten times greater in cancer cells as compared to normal cells. Abnormalities in biosynthetic regulation of lipids, especially cholesterol, are early events in tumorgenesis and are the basis for many phenotypic variations such as membrane fluidity, ion permeability, substrate transport and the activities and affinities of membrane bound enzymes and receptors.

Metastasis occurs when a tumor invades surrounding tissue and/or spreads throughout the body to begin new tumors at distant sites. Elevated cholesterol levels are associated with a number of invasive tumors. Survival rate is high for those with localized malignancy and very low for individuals when metastasis has occurred. Tumor cells are often surrounded by microvesicles. Van Blitterswijk et al. *Bio Chem. Bio Phys. Acta.* 467:309 (1974) propose that budding and shedding of these cell surface microvesicle projections occurs at plasma membrane loci that are more rigid then normal and cholesterol enriched. Besides having a role in meeting the nutritional needs of the proliferating cell, or serving as a source of excess membrane for cell division it has been proposed that these vesicles form a target for post immune response thus overloading the immune system and diverting the response from destroying the tumor cell. The shedding of these tumor vesicles may very well have a primary role in metastasis.

Japanese epidemeological studies (R.K. Cameron, et al., *Grann.*, 69:679 (1981) have reported that people who drink milk had the lowest incidence of stomach cancer, the major form of cancer in Japan. Other studies have shown a similar response for colon cancer in the American population. Inhibition of tumor cell proliferation in animal models has been reported by the use of fermented dairy products. This response has been attributed to a product of the fermentating microorganisms. (G.W. Reddy, et al., *J. Nat'l. Cancer Inst.*, 50:815 (1973); E.P.C. Esser, et al., *Milchwissenschaft*, 838:257 (1983); A.D. Ayebo, et. al., *J. Dairy Sci.*, 64:2318 (1981); L.A. Schackelford, et al., *Nutrition and Cancer*, 5:159 (1983); K.M. Shahani, et al., *J. Food Prot.*, 46:385 (1983)).

Skim milk contains two cholesterogenic inhibitors. One of these is orotic acid (OA) which inhibits acetoacyl CoA thiolase, the second enzyme in the cholesterol biosynthetic pathway and a second inhibitor IMIC (Inhibitor of Mevalonate Incorporation into Cholesterol) which prevents squalene synthetase from catalyzing the formation of squalene along the cholesterol biosynthetic pathway, (A.A. Ahmed, et al., *Atherosclerosis*, 32:347 (1979); B.J. Dull, et al., *Atherosclerosis*, 49:231 (1983); C.M. Papa, *Milchwissenschaft*, 37:257 (1982) all of which are herein incorporated by reference). Surprisingly, it has been found that since IMIC exerts its action for supressing cholesterol genesis at a site other than the normal rate-limiting enzyme, its use in tumor systems was shown to circumvent the adaptive inhibition of feedback in neoplastic cells. By preventing the mandatory requirement of cholesterol synthesis in the neoplastic cell, the growth of the tumor is supressed. Since endogenous synthesis of cholesterol is universally required in neoplastic cells for their survival, IMIC can be employed as an antineoplastic agent against virtually any neoplastic disease and is therefore applicable in the treatment of all cancers including for example, leukemias, bronchogenic carcinoma of the lung, adenocarcinomas of the colon and rectum, astrocytomas, melanomas and mammary carcinomas.

SUMMARY OF THE INVENTION

It is an object of this invention to provide a novel antineoplastic agent, designated IMIC (inhibitor of mevalanate incorporation into cholesterol), which is useful in the treatment of neoplastic disease.

Another object of the present invention is to provide a pharmaceutical composition containing IMIC which is useful in the treatment of neoplastic disease.

A further object of this invention is to provide a novel process for the preparation of IMIC.

A still further object of the present invention is to provide a method of treating neoplastic diseases.

These and other objects of this invention are achieved herein by providing a novel neoplastic agent designated IMIC having the following characteristics:

(a) is present in the retentate of dialyzed skim milk;

(b) is a molecular weight of about 165-230;
(c) is bound to a protein in the proteose-peptone fraction of milk;
(d) is non-dialyzable in the native state;
(e) is soluble in water;
(f) is insoluble in organic hydrocarbon solvents;
(g) is stable in acid stable;
(h) is not bound or retained by a $C_{18}$ or $C_8$ reverse phase HPLC columns;
(i) is not retained by a $C_{18}$ or silica gel sep pak; pak;
(j) has λ maximum absorbance at 207 and 278 nm (UV) in neutral and acidic solution and in a basic solution at 223 and 290 nm;
(k) IMIC provides a bioactive peak with a retention time of about 7.0 to about 7.8 minutes upon fractionation by HPLC (High Performance Liquid Chromatography) on a Biorad Aminex 87 WX resin column (30 cm×7.9 mm) with 0.05 $NH_2SO_4$ as the mobile phase and a flow rate of 0.7 ml/minute;
(l) IMIC provides a bioactive peak with a retention time of about 9.9 minutes upon fractionation on an HPLC Biorad Ag 50 WX-8 resin column (22 mm×30 cm) with 0.0 35 N formic acid as the mobile phase and a flow rate of about 4 ml/minute;
(m) IMIC inhibits cholesterolgenesis;

The present invention contemplates employing IMIC in compositions of pharmaceutically acceptable dosage. Futhermore, the administration of an effective amount of IMIC, provides an excellent regime for he treatment of neoplastic diseases including, for example, such as leukemias, bronchogenic carcinoma of the lung, adenocarcinomas of the colon and rectum, astrocytomas, melanomas, and mammary carcinomas.

The present invention is further characterized by a novel method for the preparation of IMIC including:
(a) heating whey at a temperature and for a time sufficient to precipitate whey proteins;
(b) removing precipitated whey proteins and retaining a supernatant;
(c) filtering the supernatant and obtaining a retentate; and
(d) recovering IMIC from the retentate;
(e) reconstituting the retentate; and
(f) repeating steps (c) and (e) a sufficient number of times to provide a condensed retentate substantially free of proteins except proteose-peptone;
(g) freeze drying the condensed retentate.

The IMIC isolate of the present invention can then be further purified by:
(a) mixing the freeze dried retentate in a methanol:formic acid:water solvent;
(b) sonicating, refrigerating and centrifuging the mixture of step (a) and retaining a supernatant;
(c) evaporating the supernatant to dryness;
(d) reconstituting the supernatant;
(e) repeating steps (c) and (d) a sufficient number of times to remove any remaining solvent;
(f) eluting IMIC from the supernatant by column chromatography;

BRIEF DESCRIPTION OF THE DRAWINGS

FIG. 1 graphically depicts the IMIC isolate eluted on an HPLC High Performance Liquid Chromatography on a Biorad Aminex 87 WX resin column (30 cm×7.9 mm) with 0.05 $NH_2SO_4$ as the mobile phase and a flow rate of 0.7 ml/minute;

FIG. 2 shows a scanning electron micrograph of P388 leukemia control cells. 5,000×, showing Filipodia and numerous blebs.

FIG. 3 shows a scanning electron micrograph of P388 leukemia control cells. 10,000×.

FIG. 4 shows a scanning electron micrograph of P388 leukemia cells treated with IMIC for 48 hours at 37° C. 5,000×, showing polysaccharide strings, fewer blebs and membrane indentations all indicating dying cells.

FIG. 5 shows a scanning electron micrograph of P388 leukemia cells treated with IMIC for 48 hours at 37° C. 10,000×.

FIG. 6 is a mass spectroscopic analysis of the IMIC isolate, showing the fragmentation pattern of the molecular weight. Height of the peak shows quantity of that fragment present in the isolate.

DETAILED DESCRIPTION OF THE INVENTION

Figure 7:
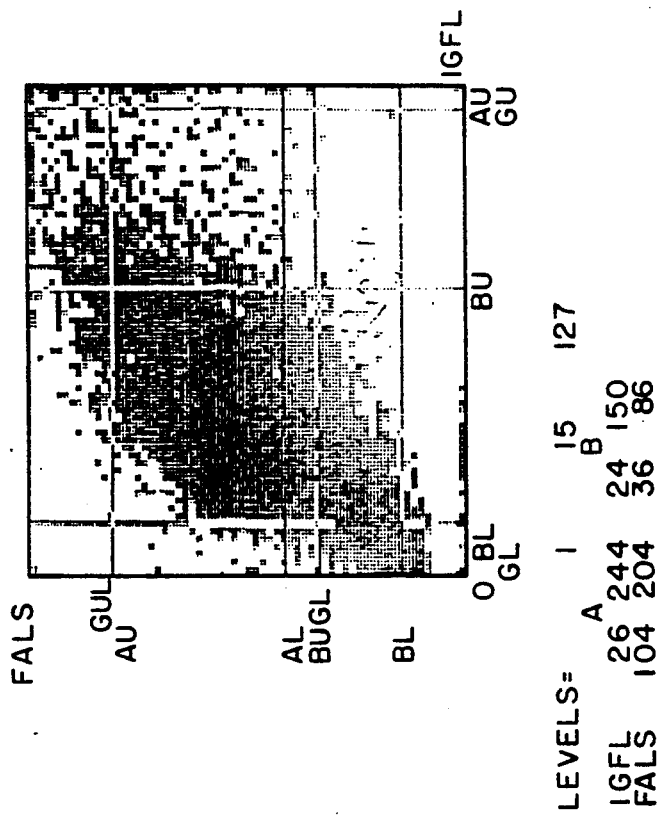
FIG. 7 depicts an actual graphic display of viable DNA in the control leukemia cells.

Skim milk contains two inhibitors of the cholesterol biosynthetic pathway. The first, ortic acid, inhibits acetoacyl CoA thiolase which catalyzes an early step in the cholesterol biosynthetic pathway. IMIC (inhibitor of mevalonate incorporation into cholesterol), the second inhibitor found as an isolate of skim milk, inhibits squalene synthesis, very late in the biosynthetic pathway of cholesterol production, by inhibiting the enzyme squalene synthetase.

Since it is postulated that neoplastic cells overcome the normal feedback of de novo cholesterol synthesis by modifying the action of the rate limiting enzyme HMG CoA reductase, a disruption of the cholesterol synthetic pathway at the point of squalene synthesis (see, Scheme I, below), i.e., beyond the point of HMG CoA reluctase in the biosynthetic pathway permits disruption of the cells ability to provide the necessary level of cholesterol. Having no other normal mechanism, to produce the requiste level of endogeneous cholesterol, the neoplastic cell is destroyed.

Since IMIC exerts its action at a site other than the normal rate limiting site, HMG CoA reductase, IMIC circumvents the adaptive mechansim of neoplastic cells. By preventing the mandatory requirement for de novo cholesterol synthesis in the neoplastic cell with IMIC, the growth of the tumor is suppressed.

The following is a schematic representation of normal endogeneous production of cholesterol:

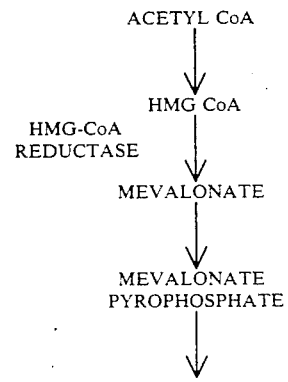

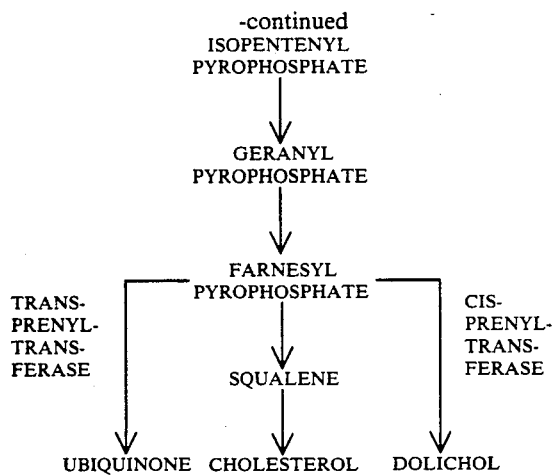

IMIC inhibits mevalonate incorporation into cholesterol and thus suppresses cholesterol formation by inhibiting the enzyme squalene synthetase along the cholesterol biosynthetic pathway. Since IMIC selectively blocks only that branch of the biosynthetic pathway responsible for cholesterol formation there is continued synthesis of other end products essential for life which are produced via the same pathway, such as dolichol which is important in glycoprotein synthesis and ubiquinone which is important in the electron transfer system. Thus, undesirable side-effects associated with other chemotherapeutic agents for cancer treatment do not occur when IMIC is used in cancer therapy. Because of the unique action of IMIC, only cholesterol formation will be reduced and the other essential end-products will still be formed. The antidote for healthy cells will be simply to feed cholesterol. Normal cells will use preformed cholesterol and function normally whereas cancer cells cannot survive utilizing any preformed cholesterol present in serum lipoprotein.

IMIC has been presently identified by the following characteristics:

(a) is present in the retentate of dialyzed skim milk;
(b) is a molecular weight of about 165–230;
(c) is bound to a protein in the proteose-peptone fraction of milk;
(d) is non-dialyzable in the native state;
(e) is soluble in water;
(f) is insoluble in organic hydrocarbon solvents;
(g) is acid stable;
(h) is not bound or retained by a $C_{18}$ or $C_8$ reverse phase HPLC columns;
(i) is not retained by a $C_{18}$ or silica gel sep pak;
(j) has λ maximum absorbance at 207 and 278 nm (UV) in neutral and acidic solution and in a basic solution at 223 and 290 nm;
(k) provides a bioactive peak with a retention time of about 7.0 to about 7.8 minutes upon fractionation by HPLC (High Performance Liquid Chromatography) on a Biorad Aminex 87 WX resin column (30 cm × 7.9 mm) with 0.05 $NH_2SO_4$ as the mobile phase and with a flow rate of 0.7 ml/minute;
(l) provides a bioactive peak with a retention time of about 9.9 minutes upon fractionation on an HPLC Biorad Ag 50 WX-8 resin column (22 mm × 30 cm) with 0.0 35 N formic acid as the mobile phase and a flow rate of about 4 ml/minute;
(m) IMIC inhibits cholesterolgenesis;

IMIC can be prepared by the following process, i.e., extraction, isolation and concentration from skim milk; or skim milk powder or from whey or dried whey.

Preferably, IMIC, the skim milk isolate of this invention can be prepared in accordance with the following procedure:

(a) adjusting the pH of skim milk to a pH sufficient to cause precipitation of the casein;
(b) removing the precipitated casein;
(c) heating the remaining whey at a temperature and for a time sufficient to cause precipitation of the whey proteins;
(d) removing the precipated whey proteins;
(e) ultrafiltering the supernatant;
(f) reconstituting the retentate to approximately the original volume with water;
(g) repeating steps (e) and (f) a sufficient number of times to leave a condensed retentate free of most proteins except proteose-peptone.
(h) freeze drying the condensed retentate.

The IMIC isolate of the present invention can then be further purified by:

(a) mixing the freeze-dried retentate with 100 ml of methanol, formic acid and water in a ratio of from 4:5:2 to 7:2:1 per gram of the freeze-dried retentate;
(b) sonicating, refrigerating and centrifuging the solution/suspension obtained in step (a) and retaining a supernatant;
(c) evaporating the product obtained in step (b) to dryness;
(d) adding distilled, deionized water to the product obtained in step (c);
(e) repeating steps c–d a sufficient number of times to remove traces of formic acid and methanol;
(f) dissolving the product obtained in step (e) in distilled water;
(g) eluting the solution obtained in step (f) on a cellulose-silicic acid column with methanol;
(h) evaporating the filtered eluate obtained in step (g);
(i) reconstituting the product obtained in step (h) in a buffer with a pH of from 7–8.
(j) filtering the product obtained in step (i).

The active ingredient IMIC of the therapeutic compositions and the compounds of the present invention exhibit excellent antineoplastic activity when administered in amounts rangeing from about 1 mg to about 10 mg per kilogram of body weight per day. A preferred dosage regimen for optimum results would be from about 2 mg to about 4 mg per kilogram of body weight per day, and such dosage units are employed that a total of from about 70 mg to about 700 mg of the active compound for a subject of about 70 kg of body weight are administered in a 24-hour period. This dosage regimen may be adjusted to provide the optimum therapeutic response and is preferably administered 2 to 4 times a day in dosages of about 150 mg per administration. For example, several divided doses may be administered daily or the dose may be proportionally reduced as indicated by the exigencies of the therapeutic situation. A decided practical advantage is that the active compound may be administered in a convenient manner such as by the oral, intraveneous (where water soluble), intramuscular or subcutaneous routes.

IMIC may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations percentage of the compositions and preparations may, of course, be varied and may conveniently be between about 25 to about 100% of the weight of the unit. The amount of active compound in such therapeutically useful compositions is such that a suitable dosage will be obtained. Preferred compositions or preparations according to the present invention are prepared so that an oral dosage unit form contains between about 150 and 400 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil or wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

IMIC may also be administered parenterally or intraperitoneally. Dispersions can also be prepared in glycerol, liquid polyethylene glycols, and mixtures thereof, and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agnets, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating IMIC in the required amount in the appropriate solvent with various of the other ingredients enumerated above, as required, follwed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previous sterile-filtered solution thereof.

As used herein, "pharmaceutically acceptable carrier" includes any and all solvents, dispersion media, coating, antibacterial and antifungal agents, isotonic and absorption delaying agents, and the like. The use of such media and agents for pharmaceutical active substances is well knwon in the art. Except insofar as any conventional media or agent is incompatible with the active ingredient, its use in the therapeutic compositions is contemplated. Supplementary active ingredients can also be incorporated into the compositions.

For a better understanding of the present invention together with other and further objects. Reference is made to the following examples.

EXAMPLE 1

I. Isolation of IMIC

A. Preparation of Enriched Isolates of IMIC

1. Approximately 120 liters of skim milk was obtained;
2. The pH was adjusted to about 3.5-4.7 or sufficient to cause casein precipitation;
3. The whey was heated at 80°-100° C. for 30-60 minutes, then the material was held at 2°-8° C. for approximately 10 hours; and the precipitated whey proteins were removed by filtration;
4. The supernatant was then passed through an Abcor ultra-filter at 110° F., with an inlet pressure of 50 PSI and an outlet pressure of 20 of PSI;
5. The retentate was reconstituted to the original volume with warm water and re-circulated through the ultra filter. The process was repeated 5 times which left a condensed retentate free of most proteins (except proteose-peptone) lactose, minerals and other soluble material;
6. The condensed retentate (proteose peptone fraction) was stored in the frozen state; At this point the Freeze Dried Base (FDB) is obtained;
7. One gram of solids which was obtained by freeze drying the retentate was mixed with 100 ml of methanol:formic acid:water (7.2.1);
8. This solution/suspension was sonicated for approximately 30-40 minutes, refrigerated approximately 4 hours, and then centrifuged for approximately 25 minutes at 1000 g at 4° C.;
9. The filtered supernatant was rotary evaporated to dryness; At this point IMIC working base fraction (IWBF) was obtained;
10. Distilled, deionized water was added to the sample which was again rotary evaporated to dryness. This was repeated 5 times to insure complete removal of traces of formic acid and methanol. This material was suitable for attempting further fraction employing HPLC (see section B);

11. For preparing the isolate for use in in vitro and in vivo studies (the sterile inhibitor research sample IRF) the material was dissolved in approximately 10 ml of distilled water;

12. The solution was placed on a cellulose-silicic acid column and eluted with approximately 200 ml of methanol;

13. The filtered eluate was rotary evaporated to dryness, reconstituted in appropriate buffer, pH adjusted to from 7 to 8 and filtered through through a 0.45 u and 0.2 u tissue culture filtering flask into a sterile container;

14. The sterile fraction was stored frozen.

B. Further Purification

The Active isolate was fractimated by HPLC on a Biorad Aminex resin column (30 cm×7.9 mm) with 0.05 $NH_2SO_4$ as the mobile phase. The separation was conducted at 1200 PSI and at a flow rate of 0.7 ml/minute. The enriched fraction either before or after the cellulose column described in section A may be injected. Bioassays using rat liver slices to verify the presence of IMIC strongly suggest that the peak with a retentation time of from 7.0 to 7.8 and most likely 7.52 minutes is the active component (See FIG. 1). Sulfuric acid from the mobile phase is separated from the active component on a Biorad Ag 50 WX-8 gravity flow resin column. The column is 25 cm×1 cm with a flow rate of 1 ml per minute. Formic acid (0.02 M) serves as the mobile phase. Sulfuric acid elutes in 22 minutes followed directly by the active component. Formic acid (from mobile phase) was removed from the compound by rotary evaporation at 50° C. The material may also be fractionated on an HPLC Biorad Ag 50WX-8 resin column (22 mm×30 cm) with 0.035 N formic acid as the mobil phase. With a flow rate of 4 ml/minute the component shows a retention time of 9.9 minutes. The IMIC isolate does not bind to nor is it retained by a $C_{18}$ or $C_8$ reverse phase HPLC columns or a $C_{18}$ or silica gel sep pak. These columns normally bind non-polar compounds. IMIC is believed to have an aromatic structure and is probably pyrimidine-like in structure due to its absorption maximum, its mass speetrograph (FIG. 6) and its behavior in the aforementioned chromatographic system.

C. Preparation of Freeze-dried Base (FDB)

Freshly skimmed milk is the starting material. The pH was adjusted to cause precipitation of the casein. The whey was heated to 90° C. and filtered. The fraction is then put through an Abcor spiral wound membrane system. The latter was employed to remove soluble materials and lactose from the proteose-peptone fraction. After ultrafiltration, the proteose-peptone retentate was frozen in homogenous 950 ml lots for freeze drying in a Stokes Model 902-001 freeze drier at a later date.

D. Extraction of the IMIC Enriched Fraction

Initially, 10 grams of FDB was added to 700 ml methanol, 200 ml formic acid and 100 ml water. All reagents were distilled in glass prior to use. This mixture was sonicated for 35 minutes and stored for 12 hours at 4° C. The mixture was then resohicated and centrifuged at 10,000× for 25 minutes in a Beckman J2-21 centrifuge. The supernate was collected and filtered through whatman #2 filter paper. The filtrate was rotary evaporated at 55° C. until dryness. To rename traces of formic acid and methanol used in isolating the inhibitory fraction, distilled water (100 ml/gram FDB) was added to the flask and rotary evaporated off. This was repeated five times to assure complete removal of any traces of solvent.

A volume of (10 ml/gram of FDB) distilled water was added to the dry, solvent-free inhibitor isolate. This volume was called the inhibitor working base fraction (IWBF), and was used for different liver slice experiments or further treated for in vivo or in vitro experiments.

E. Concentration of IMIC Fraction

The IMIC fraction was manipulated to remove most of the protein and to further concentrate the inhibitor. A cellulose-silicic acid column was employed for protein removal. These columns were 25 cm long, containing approximately 3 cm of resized silicic acid on the bottom and the remaining 23 cm contained crystalline methylcellulose. Both column materials were reconstituted in 100% methanol. About 200 ml of 100% methanol was allowed to drain through the columns to remove any foreign materials. Ten ml of the IWBF was spotted on the column and eluted with a 50:50 mixture of methanol and water. The mixture was passed through the column at a flow rate of one drop per three seconds. Compressed nitrogen was used to establish the flow rate. After collecting 200 ml from each column, the effluent was filtered through a Whatman #2 filter and then rotary evaporated to dryness. After drying, the IMIC isolate was reconstituted with (10 ml/gram FDB) physiological buffered saline (PBS) or Ringers Locke solution. This solution was then adjusted to pH 7.4 and filtered through Nalgene tissue culture filters with pore sizes of 0.45 u and 0.2 u.

EXAMPLE 2

In vivo rat liver slices were used to verify the presence of IMIC. Animals were killed by cervical dislocation. The left unsegmented lobe of the the liver was removed and placed in Lakshamanan buffer (M.R. Lakshamanan, *Biochem. Bio Phys. Res. Comm.*, 50:704 [1973].) Liver slices, 0.8 mm thick, were obtained. Slices were trimmed to 100–110 mg and placed into 25 ml incubation vials. Added to each vial was 2.2 ml of Lakshamanan buffer, 500 ul of a buffer containing 1.3 mg ATP and 3.8 mg NAD, 100 ul of a 10 uCi/ml [5-$^3$H-(N)]-mevalonate (apx 100,000 CPM) and 200 ml of treatment. All treatments were run in triplicate. Each liver slice incubation was performed with an incubation control and an extraction control. The incubation control vial contained the same reagents as the treatment vials, except 200 ul of Lakshamanan buffer was used in place of a treatment. The isolation and extraction control was similar to the incubation control except that it used 200 ul of distilled water that had gone through each treatment step used to prepare the inhibitor fraction.

The liver slices were incubated in a Dubinhoff metabolic shaker (GCA; Precision Scientific, Chicago, IL.) at 37° C. for three hours in an atmosphere of 95% $O_2$ and 5% $CO_2$. The incubation was terminated by the addition of 4 ml of 15% KOH in ethanol and 0.5 mg of non-radioactive cholesterol carrier. At the end of three hours of saponification at 75° C., cholesterol was successively extracted with 10, 8 and 6 ml of distilled hexane. After combining the aliquots, the hexane was evaporated completely. Cholesterol residue that remained after solvent evaporation was dissolved in 5 ml hexane, after which 1 ml samples were removed and dispersed into scintillation vials. Following the removal of the solvent, scintillation fluid was added to each vial.

Each new preparation of IMIC from the ultrafilter and each successive column preparation was checked for bioactivity in this manner. Incubation controls, isolation and extraction controls were also checked on each new inhibitor preparation to assure inhibition was due to the treatment and not to materials used in the extractions.

Table 1 illustrates the effect of IMIC, and various dilutions obtained from Example 1 on the incorporation of $^3$H-mevalonate into cholesterol when incubated with 100 mg rat liver slices at 37° C. for 3 hours in Lakshamanan buffer.

Table 2 illustrates the effect of IMIC, and various purification methods according to Example 1 on $^3$H-mevalonate incorporation into cholesterol when incubated with 100 mg rat liver slices at 37° C. for 3 hours in Lakshamanan buffer.

Table 3 illustrates the effect of eluent fractions from cellulose-silicic acid column treatment according to Example 1 on $^3$H-mevalonate incorporation into cholesterol when incubated with 100 mg rat liver slices at 37° C. for 3 hours in Lakshamanan buffer.

The data in Table 3 shows that the bulk of the IMIC fraction eluded in the first 150 ml of the column. When the bioactive fraction was observed on TLC plates it visually demonstrated less contamination. Because the isolate was to be used with viable cells, a sterile fraction was necessary. Tissues culture filters with pore sizes 0.45 u and 0.2 u were used to obtain the sterile fraction. Studies were performed which demonstrated that autoclaving the IMIC at 121° C., 18 PSIG for 15 minutes yielded a sterile fraction, but the use of the tissue culture filters removed additional extraneous matter with only a small reduction in the inhibitory actions of the IMIC.

Thus, in rat liver slice assays, use of the IMIC fraction yielded consistant inhibition of cholesterol synthesis of 70-80%. It was determined that a 1:10 dilution reduced the inhibition by IMIC to 46% (Table 1). It was noted that the IMIC preparation had a shelf life of 4 months. After this time results would vary using the same IMIC fraction. Preparation and dilution of the IMIC fraction was standardized at this point. It was used at a volume based on a known weight of skim milk proteose-peptone fraction.

EXAMPLE 3

The following Microsomal Squalene Synthetase in vitro Bioassay was conducted to show the inhibitory effect of the IMIC isolate on the incorporation of 3H-farnesyl pyrophosphate into squalene, the point at which squalene synthetase is present.

The reaction mixture for measuring the formation of 1-[$^3$H]-presqualene pyrophosphate and or $^3$H-squalene is described in Table 4. The pH was adjusted to approximately 7.4 after dissolution of the phosphate buffer and prior to enrichment with the remaining components. One thousand five hundred fifty nmol (125,000 cpm) of 1-[$^3$H]-farnesyl pyrophosphate, mixed isomers (specific activity=144 u Ci/nmol), were added as the substrate for the reaction. This corresponds to 550 nmol (35.7%) trans, trans isomer. Two hundred microlitres of buffer were replaced by 200 ul inhibitor sample when inhibition studies were performed. The reaction was initiated by the addition of 100 ul of a microsomal preparation, 5.3 mg/ml protein (530 ug protein/vial) as determined by the method of Lowry, et al. Immediately, the reaction mixture was flushed with nitrogen and stoppered. Anaerobic incubation was continued for 60 min. at 37° C. under mild agitation.

ISOLATION OF SQUALENE

The incubation reaction was terminated with 3 ml of 20% isopropanolic KOH. At this time 0.5 mg of carrier squalene and farnesol (Sigma Chemical Co.) was added to the flask. The mixture was saponified 12 h at 50° C. The saponified mixture was diluted with 20 ml of distilled water and extracted 3 times with 30 ml portions of petroleum ether. The ether extracts were combined and evaporated to dryness. Five ml of petroleum ether were added to re-dissolve the residue and 2-1.0 ml aliquots were scanned for radioactivity. The remaining 3 ml were retained for fractionation of the products.

The results as set forth in Tables 5 and 6 show that IMIC inhibited the formation of squalene from farnesyl pyrophosphate thus evidencing the fact that IMIC acts at the locus of squalene synthetase along the biosynthetic pathway.

In Vitro and in vivo experiments were performed using P388 leukemia cells to determine the effects that IMIC had on P388 leukemia tumor cells.

EXAMPLE 4

Initial Preparation and Maintenance of the Culture

P388 leukemia cells frozen at −80° C. were placed in 32° C. RPMI 1640 media. After thawing, cells were centrifuged at 1000 rpm for 10 minutes. The supernate was discarded and the pellet of cells was suspended in 15 ml of fresh RPMI 1640 media with 10% FBS. After 48 hours, the non-attached cells were removed from the flask and placed in new media. When each flask reached a concentration of $10^6$ cells/ml, all flasks were combined and diluted with RPMI to $10^5$ cells/ml. Every 48 hours, cells were transferred and diluted to $10^5$ cells/ml with fresh RPMI 1640 and 10% FBS.

Because of the growth requirements of the P388 cells, new media was added when the cells reached a concentration of $10^6$ cells/ml. To assure continued growth of the cells, 20 ml of $10^6$ cells were added to 40 mls of 37° C. RPMI with 10% FBS for cell transfers and cell culture experiments. Culture flasks were placed on tissue culture shakers (125 rpm) for 48 hours at 37° C. To assure the purity of the cell line, P388 cells were centrifuged and the supernate was dispensed into brain heart infusion broth to check for contamination of the P388 culture.

Cells were counted by removing 0.5 ml from a well-mixed suspension of cells and adding to it 0.1 ml of 0.4% trypan blue stain (Gibco Labs). Trypan blue is a standard tissue culture stain that discriminates dead cells from live cells on the basis of whether or not the cells contain the stain. The live cell can remove the stain, while the dead cell cannot. Cells were counted between 5-15 minutes after stain addition. Stained cells were placed on an AO model hemacytometer (Fisher Scientific). Cells on three diagonal grids of the hemacytometer were counted and averaged. By multiplying this number of $10^4$, one obtained the number of cells/ml. Dilutions were made when necessary to aid in counting.

REAGENTS

All chemicals were reagent grade and purchased from Sigma Chemical Co., St. Louis, Mo. Organic solvents were reagent grade and distilled in glass before use. $^3[H]$-mevalonate was purchased from New England Nuclear Research Products, Boston, Mass. Fisher scintiverse E was the universal scintillation cocktail. All radioactivity measurements were performed on a Packard tri-carb liquid scintillation spectrometer (model 3320). Quench corrections were conducted with an external standard.

ANIMALS

Male wistar rats weighing 200-300 grams were used as liver donors for liver slice incubations. Commercial rat chow and water were provided ad libitum. Animals were acclimated to 12-hour light an dark cycles for at least one week prior to sacrifice which occurred during the midpoint of the dark cycle.

In tumor cell experiments, male DBA/2 and $B_6D_2F_1/J$ mice were purchased from Jackson Labs, Bar Harbor, Me. Mice were 26-27 days old. Animals were held on 12-hour light and dark cycles. Purina mouse chow was supplied ad libitum. Each treatment group contained six mice while the control groups contained eleven mice as specified by the National Cancer Instituted, Instruction 14 (NCI-14), protocols for screening were as according to (R.I. Geran, et al., *Cancer Chemoth. Rep.*, 31 (1972) and screening and evaluation of antitumor agents were as according to A. Golding, et al., *Cancer Medicine*, Ch.35, Lea and Febiger Philadelphia, PA, (1982) and G. Klein, et al., *J. Natl. Cancer Inst.*, 14:229 (1953).

CELL CULTURE

All cell culture methods were modeled after Ramu, et al., *Cancer Treatment Rep.*, 68:637 (1984). Gentamycin was purchased from Sigma Chemicals, 1640 media (RPMI 1640) and fetal bovine serum (FBS) were obtained from Gibco Laboratories Sterile 23-gauge needles and tuberculin syringes were purchased from Arther Thomas Co., Philadelphia, Pa. P388 (945) leukemia ascetes tumor cells were obtained from the NCI Frederick Cancer Research Facility. Cells were kept at $-80°$ C. until research began.

DNA DETERMINATION

Ten ml of the ascetic fluid containing P388 cells from each experimental treatment were removed after incubation and frozen for subsequent DNA determination. Increase in DNA is a measure of cell growth. A standard DNA curve was developed using calf thymus DNA (Boehringer Mannheim) via the procedure of Shelton, et al., *J. Natl. Cancer Inst.*, 44:1201 (1970) and Schneider, *J. Bio. Chem.*, 161:293 (1945). Once the tumor cells were isolated from the animal or from cell culture, they were subjected to standard procedure for DNA determination. The addition of 2 ml diphenylamine gave a color change in the DNA extract, where the intensity of the blue color was proportional to the amount of DNA present. The absorbance was measured on a Bausch and Lomb Spectrometer 20 at 600 nM, then interpolated on the standard DNA curve to yield ug DNA/ml of the leukemic cells.

EXAMPLE 5

In Vitro Studies

In vitro experimentation is worthwhile because the cholesterol synthesis inhibiting factor could be applied directly to the cellular environment.

In vitro studies were carried out to determine the effects various treatments including IMIC had on P388 leukemia cells in culture. Results were shown in terms of the numbers of viable P388 cells remaining and/or DNA content and/or incorporation of $^3H$-mevalonate into cholesterol. Tables 7, 8 and 9 show experimental protocol for the in vitro experiments 1, 2 and 3. Results are shown in corresponding Tables 7a, 8a and 9a.

The results presented in Table 7a show a dramatic effect of the IMIC component on leukemic cells in vitro. 98-100% of the P388 cells were killed as a result of the addition of the IMIC fraction alone. IMIC when combined with orotic acid yielded similar results. In experiment 1, the IMIC and orotic acid treatment had the same total amount of each component as experiment 2 (Table 8a). The volume of buffer containing these components added in experiment 1 was 8 ml, whereas the amount added in experiment 2 was 2 ml. The IMIC alone had 90-100% reduction in the numbers of viable P388 cells in experiments 1 & 2. At one quarter the standard concentration of IMIC, only 16% reduction in the numbers of P388 cells was observed. This is consistent with the dilution experiment in the IMIC bioactivity section. Combinations of IMIC and orotic acid showed variable results indicating some interaction on the cells. Only IMIC clearly demonstrated a result.

Orotic acid alone had a stimulatory effect in experiments 1 & 2. From the data shown the orotic acid does not contribute to the inhibition of P388 cell numbers in vitro.

Experiment 3 (Table 9a) measured two other parameters in addition to the effect on the numbers of viable P388 cells. The effect on the DNA content on the P388 cells and their incorporation of $^3H$-mevalonate into cholesterol was studied. DNA content of the P388 cells is an indicator of tumor growth.

In these same studies, the amount of $^3H$-mevalonate incorporated into cholesterol was reduced considerably. All three cell culture experiments showed strong reduction in the numbers of cells (65-100%), and this reduction in the numbers of P388 cells is supported by a decrease in the DNA content of the cells (30-38%).

In vitro experiments showed 70-100% reduction in numbers of viable P388 leukemic cells when incubated with the IMIC fraction at 37° C., for 48 hours in cell culture. Under the same conditions, orotic acid (OA) the other cholesterol-genic inhibitor present in skim milk did not show consistant trends.

Scanning electron microscopy was conducted to illustrate the effects that the various treatments had on P388 leukemia cells. The Electron micrographs show that leukemia cells treated with IMIC are dying.

The procedure for scanning electron microscopy is as follows:

Glass microscope slides were covered with poly-L-lysine (Sigma Chemical) and allowed to stand at room temperature for one hour, after which the slides were blotted with lens paper. The slide was then flooded with P388 cells after receiving the various treatments and allowed to stand for 2 hours. Slides were then immediately placed in fixative (2% gluteraldehyde, (0.1 M) cacodylate at pH 7.4 and 0.1 m sucrose) until analysis.

Cells were rinsed with buffer (0.1 M cacodylate at pH 7.4 and 0.1 M sucrose) and prepared for gradual alcohol dehydration. The dehydrated samples were immediately critically point dried (CPD) in a Polaron E-3000. The CPD procedure consisted of four 15-minute exchanges of bone dry $CO_2$ at 800 PSIG 19° C). Upon completion of the four exchanges, the chamber jacket was heated, bringing the chamber conditions beyond the critical point of $CO_2$ (1100 PSIG, 34° C.). The chamber was drained and the dried samples on the cover slips were attached to aluminum disks by two sided sticky tape. Silver tape ensured conductance of the disk. All disks were gold sputter coated (280 A thick) and placed in a dessicator until viewing.

Each disk was viewed in an ISI-60 scanning electron microscope with a 150 A emmission current at 30 KV. Photographs were taken with a Polaroid 545 land camera with 52 series polaroid film.

FIGS. 2-5 illustrate P388 leukemic cells from in vitro experiment 2. Micrographs of control and IMIC treated cells are shown. Control samples in FIGS. 2 and 3 show healthy P388 cells. These cells show the ruffled membrane and fillopodia characteristic of cells in late $G_1$ phase of the cell cycle. The IMIC treated cells (FIGS. 4 and 5) have rough looking membranes, are smaller and have dense strands of polysaccharides throughout the membrane, a characteristic of dying cells.

Figure 8:
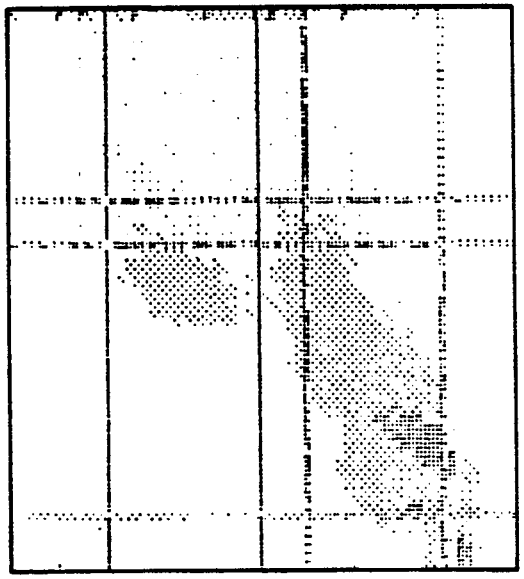
FIG. 8 depicts the actual graphic display of viable DNA for leukemia cells incubated with added IMIC.

The micrographs demonstrate the effect of IMIC on P388 cells. IMIC treated cells showed large amounts of polysaccharide throughout the medium. IMIC cells were less in numbers. As illustrated in FIGS. 7 and 8, the number of live P388 leukemia cells incubated with IMIC for 48 hours in vitro is dramatically reduced.

EXAMPLE 6

In vivo experiments were divided into two categories: feeding studies (experiments 1 & 2; in Tables 10 & 11), and injection studies (experiments 3-6; in Tables 12, 13, 14 and 15). Feeding studies involved giving the animal fresh proteose-peptone fraction daily, allowing an acclimation period to the proteose-peptone before P388 injections began. Mice were sacrificed at various periods to determine the effects the feeding of the fraction had on the numbers of viable P388 cells remaining and/or DNA content.

The injection studies involved daily IP injections of various treatments for 6 days, beginning 24 hours after the animals received injections of $10^6$ P388 cells IP. Animals were sacrificed at various time periods to determine what effects injections had on the numbers of viable P388 cells and/or DNA content.

Feeding studies demonstrated 41-59% reduction in viable P388 cell numbers, while injection studies demonstrated reduction in viable P388 cell numbers of 20-90%.

The interperitoneal (IP) cavity of the mouse was doused with 70% alcohol. All surgical instruments were kept in 90% alcohol and flamed before use. After cutting back the fur, a sterile 1 ml tuberculin syringe with a 23 gauge needle was used to inject 1 ml of sterile PBS into the abdominal cavity. The IP membrane was lifted and relaxed several times to mix and resuspend ascetes cells in the IP cavity. A new syringe was used to remove as much ascitic fluid as possible. This procedure was repeated several time. A small opening was then cut in the IP membrane and 2 ml of PBS was introduced into the cavity. A new syringe was used to remove the ascetic fluid behind the organs. A total of 8-10 ml was obtained and then centrifuged at 1760 rpm. The supernate was discarded and 1 ml of sterile PBS was added to the pellet. The samples were vortexed to an even distribution and 0.5 ml of cells were mixed with 0.1 ml of 0.4% trypan blue stain as previously described. Inhibition was determined by comparing the live cell numbers in the treatments to the live cell numbers of the controls.

Tables 10 & 11 show experimental protocol for feeding studies in vivo experiments 1 and 2, and Tables 12, 13, 14 and 15 give experimental protocol of the injection studies in vivo experiments 3-6.

Results of in vivo experiments 1-6 are seen in Tables 10a, 11a, 12a, 13a, 14a and 15a. In in vivo experiments, two types of mice were used as hosts for the P388 cells.

A. Feeding Studies

Experiments 1 & 2 (Tables 10a & 11a) dealt with feeding the proteose-peptone fraction to mice which were injected IP with the P388 cells. The purpose was to determine whether the active IMIC component could enter the digestive tract, be absorbed and diffuse throughout various body compartments. A period of 9 days (experiment 2) and 14 days (experiment 1) was allowed for the acclimation of the mice to drinking the fraction, and they continued drinking the fraction until they were sacrificed. Mice readily took to drinking this material. Experiment 1 provided data on the effect on IMIC on the numbers of cells and DNA content. Inhibition on the numbers of cells increased from 41% to 68% during weeks 1 and 2, but declined to 53% in week 3. Feeding experiment 2 used the $B_6D_2F_1/J$ mouse and showed reduction of 59% in numbers of cells 1 week after IP injection of P388 cells.

B. Injection Studies

In experiments 3 & 4 (Tables 12a & 13a) the DBA/2 mouse was used. In experiment 3, the orotic acid and IMIC treatment that showed stimulation in the cell culture experiments showed inhibition in vivo at 10 days post-P388 injection. This may be due to use in a host system.

Table 13a shows data which repeats experiment 3. Viable cell numbers were reduced nearly 40%. Changes in the DNA content were less dramatic, possibly due to the small numbers of cells that could be obtained from each treatment. DNA was determined on total cells with no differentiation between viable and non-viable cells.

$B_6D_2F_1/J$ mice were used in experiments 5 & 6 (Tables 14a & 15a). Inhibition of 20-40% is shown in Tables 14a & 15a.

When examining the actions of IMIC in vitro, a major reduction in the number of viable P388 cells was demonstrated by the IMIC component. It was also shown (Table 10a) that mevalonate incorporation into cholesterol was reduced in IMIC's presence and less measurable DNA was present.

Feeding studies in both strains of mice showed good inhibition (41 & 59%), demonstrating the ability of the IMIC component to pass through the intestine into the IP cavity. This suggests applications in treatment of metastasis.

Results of 90-100% inhibition of P388 cell numbers in cell culture were consistently found. $^3$H-mevalonate incorporation into cholesterol was determined to be lower in the IMIC treated cells. In vivo two types of experiments were performed. Feeding studies demonstrated 41-59% reduction of P388 leukemia cell numbers while treatment injection studies demonstrated reduction in P388 cell numbers of 20-39% and 40-90% in $B_6D_2F_1/J$ and DBA/2 mice, respectively. Both the in vivo and in vitro experiments show that the IMIC fraction inhibits tumor growth and proliferation through its inhibition of cholesterol synthesis.

TABLE 1

Effect of IMIC and various dilutions obtained from Example 1 on the incorporation of $^3$H-mevalonate into cholesterol when incubated with 100 mg rat liver slices at 37° C. for 3 hours in Lakshamanan buffer.

| Dilution | Average CPM +]SD | % Inhibition based on Incubation Control |
|---|---|---|
| Incubation Control | 24000 ± 4800 | — |
| Filtered Inhibitor (no dilution) | 3700 ± 210 | 85% |
| 1:10 | 13000 ± 3400 | 45% |
| 1:50 | 23000 ± 1600 | — |
| 1:100 | 24000 ± 620 | — |

CPM = counts per minute (a measure of radioactivity)
SD = standard deviation

TABLE 2

Effect of IMIC, various purification according to Example 1 on $^3$H-mevalonate incorporation into cholesterol when incubated with 100 mg rat liver slices 37° C. for 3 hours in Lakshamanan buffer.

| | Average CPM + SD | | | % Inhibition | |
|---|---|---|---|---|---|
| Purification Method | Incubation Control CPM | Extraction Blank CPM | IMIC Blank | Based on Incubation Control | Based on Extraction Blank |
| Cellulose TLC Plate | 21000 ± 3700 | 8800 ± 3400 | 3900 ± 1400 | 82% | 55% |
| Cellulose-silicic Acid Column | 31000 ± 1100 | 34000 ± 3500 | 4600 ± 370 | 85% | 85% |
| Cellulose-silicic Acid Column with .2 u filter | 1500 ± 360 | 1800 ± 310 | 450 ± 160 | 69% | 74% |

CPM = counts per minute (a measure of radioactivity)
SD = standard deviation

TABLE 3

Effect of eluent fractions from cellulose-silicic acid column treatment according to Example 1 on $^3$H-mevalonate incorporation into cholesterol when incubated with 100 mg rat liver slices at 37° C. for 3 hours in Lakshamanan buffer.

| Fraction Off Column | Incubation Control CPM | Extraction Blank CPM | IMIC CPM | Based on Incubation Control | Based on Extraction Blank |
|---|---|---|---|---|---|
| 1$^{st}$ 150 ml | 500 ± 2200 | 34000 ± 3500 | 31000 ± 1100 | 85% | 85% |
| 2$^{nd}$ 150 ml | 33000 ± 950 | 34000 ± 950 | 31000 ± 1100 | — | |

CPM = counts per minute (a measure of radioactivity)

TABLE 4

The Composition of Buffer Used as Incubation Media in the Squalene Synthetase Assay.

| Ingredient | Quantity |
|---|---|
| KH$_2$PO$_4$ | 100 μmol/ml |
| MgCl$_2$ | 5 μmol/ml |
| NADPH | 1 μmol/ml |
| Nicotinamide | 30 μmol/ml |
| KF | 10 μmol/ml |
| BSA | 2 mg/ml |
| β-D (+) glucose | 30 μmol/ml |
| Glucose Oxidase | 0.009 Units/ml |

Final pH was adjusted to pH 7.4 with 1.0 N KOH.
Total incubation volume was 2.0 ml.

TABLE 5

Effect of IMIC isolate onthe Incorporation of $^3$H-Farnesyl pyrophophate into squalene by Pooled Rat Liver Microsomal Preparations During a 60 minute Incubation

| | Radiolabeled Squalene formed | | |
|---|---|---|---|
| Experiment | Control | Inhibitor added | % Change |
| 1 | 14100 ± 550 | 9820 ± 1350 | −30 |
| 2 | 20500 ± 2000 | 11800 ± 2300 | −42 |
| 3 | 1450 ± 166 | 960 ± 200 | −34 |
| 4 | 7900 ± 1000 | 4200 ± 1000 | −47 |
| 5 | 2800 ± 730 | 760 ± 140 | −73 |
| 6 | 6900 ± 250 | 3900 ± 150 | −39 |

TABLE 6

Effect of IMIC Isolate and HPLC fraction on the Incorporation of 3$_h$-Farnesyl pyrophosphate into squalene by pooled Rat Liver Microsomal Preparations During a 60 Minute Incubation

| Experiment | CPM Squalene | % Change |
|---|---|---|
| Control | 4100 | |
| IMIC Isolate | 2700 | −32 |
| HPLC - Blank | 4100 | |
| HPLC - Component | 3000 | −25 |
| Control | 48% | |
| IMIC Isolate | 3400 | −29 |
| HPLC Blank | 5000 | |
| HPLC Component | 3600 | −25 |

CPM = counts per minute (a measure of radioactivity)

TABLE 7

In vitro experiment 1. Experimental design to determine the effect of various treatments onthe numbers of P388 leukemia cells surviving incubation at 37° C. for 48 hours.

| Treatment | ml Treatment Added | ml P388 Cells Added (10$^6$ cells/ml) | RPMI 1640 and 10% FBS Added |
|---|---|---|---|
| IMIC[1] | 8 ml | 20 ml | 40 ml |
| Orotic Acid[2] | 8 ml | 20 ml | 40 ml |
| Orotic Acid and IMIC[3] | 8 ml | 20 ml | 40 ml |

TABLE 7-continued

In vitro experiment 1. Experimental design to determine the effect of various treatments on the numbers of P388 leukemia cells surviving incubation at 37° C. for 48 hours.

| Treatment | ml Treatment Added | ml P388 Cells Added ($10^6$ cells/ml) | RPMI 1640 and 10% FBS Added |
|---|---|---|---|
| Control[4] | 8 ml | 20 ml | 40 ml |

[1]Prepared as follows: 10 grams of FDB was added to 700 ml/200 ml/100 ml (MeOH/HCOOH/H$_2$O) following the procedures in Example 1. The IRF was reconstituted with (10 ml/gram FDB) Ringers Locke solution. The IRF was adjusted to pH 7.4 and filtered through a .45μ and .2μ tissue culture filter.
[2]Prepared as follows: 25 mg orotic acid was added to 100 ml of Ringers Locke solution, then autoclaved at 121° C., 18 PSIG for 15 minutes. Treatment was adjusted to pH 7.4 and filtered through a .45μ and .2μ tissue culture filter.
[3]Prepared as follows: 10 grams of FDB was added to 700 ml/200 ml/100 ml (MeOH/HCOOH/H$_2$O) following the procedures in Example 1. The IRF was reconstituted with (10 ml/gramFDB) Ringers Locke solution. Four ml of orotic acid was added to four ml IRF, for a total of 8 ml in the treatment. Treatment was filtered through a .45μ and .2μ tissue culture filter.
[4]Prepared as follows: 8 ml of Ringers Locke solution was added as treatment.

TABLE 7a

In vitro experiment 1. Effect of various treatments upon viable P388 leukemia cells ($10^6$ cells/ml) surviving in cell culture after 48 hours at 37° C.

| Treatment | Numbers of Viable P388 Cells/ml | % Inhibition Based on Ringers Locke Control |
|---|---|---|
| Carry Culture | $1.10 \times 10^6 \pm 7100$ | — |
| Control | $.74 \times 10^6 \pm 880$ | — |
| IMIC | Less Than 1000 | 100% |
| Orotic Acid | $.66 \times 10^6 \pm 3500$ | 11% |
| IMIC and Orotic Acid | Less Than 1000 | 100% |

TABLE 8

In vitro experiment 2. Experimental design to determine the effect of various treatments on the numbers of P388 leukemia cells surviving incubation at 37° C. for 48 hours.

| Treatments | ml Treatment Added | ml P388 Cells Added ($10^6$ cells/ml) | RPMI 1640 and 10% FBS Added |
|---|---|---|---|
| IMIC-A[1] | 2 ml | 20 ml | 40 ml |
| IMIC-B[2] | 2 ml | 20 ml | 40 ml |
| Orotic Acid[3] | 2 ml | 20 ml | 40 ml |
| Orotic Acid and IMIC[4] | 2 ml | 20 ml | 40 ml |
| PBS Control[5] | 2 ml | 20 ml | 40 ml |

TABLE 8-continued

In vitro experiment 2. Experimental design to determine the effect of various treatments on the numbers of P388 leukemia cells surviving incubation at 37° C. for 48 hours.

| Treatments | ml Treatment Added | ml P388 Cells Added ($10^6$ cells/ml) | RPMI 1640 and 10% FBS Added |
|---|---|---|---|
| Extraction and Isolation Blank[6] | 2 ml | 20 ml | 40 ml |

[1]Prepared as follows: 10 grams FDB was added to 700 ml/200 ml/100 ml (MeOH/HCOOH/H$_2$O) following the procedures in Example 1. The IRF was reconstituted with (2.5 ml/gram FDB) physiological buffered saline (PBS). The pH was adjusted to 7.4 and filtered through a .45μ and .2μ tissue culture filter.
[2]Prepared as follows: Same as #1, except the IRF was reconstituted with (10 ml/gram FDB) PBS.
[3]Prepared as follows: 25 mg orotic acid was added to 100 ml PBS and autoclaved. The treatment was adjusted to pH 7.4 and filtered through a .45μ and .2μ tissue culture filter.
[4]Prepared as follows: 4 grams of FDB was added to 250 ml/80 ml/40 ml (MeOH/HCOOH/H$_2$O) following the procedures in Example 1. The IRF was reconstituted with 10 ml/gram FDB) orotic acid. Orotic acid was prepared by adding 25 mg orotic acid to 25 ml PBS. Treatment was adjusted to pH 7.4 and filtered through a .45μ tissue culture filter.
[5]Prepared as follows: 2 ml of PBS was added as treatment.
[6]Prepared as follows: Same as #1, except water added instead of FDB.

TABLE 8a

In vitro experiment 2. Effect of various treatments upon viable P388 leukemia cell ($10^6$ cells/ml) surviving in cell culture after 48 hours at 37° C.

| Treatment | Numbers of Viable P388 Cells/ml | % Inhibition Based on PBS Control | % Inhibition Based on Extraction Blank |
|---|---|---|---|
| Garry Culture | $1.22 \times 10^6 \pm 95000$ | — | — |
| PBS Control | $1.23 \times 10^6 \pm 64000$ | — | — |
| Extraction and Isolation Control Blank | $.86 \times 10^6 \pm 38000$ | 31% | — |
| IMIC-A | $.02 \times 10^6 \pm 21000$ | 98% | 97% |
| IMIC-B | $1.03 \times 10^6 \pm 81000$ | 16% | Stimulation |
| Orotic Acid | $1.90 \times 10^6 \pm 7100$ | Stimulation | Stimulation |
| Orotic Acid and IMIC | $.99 \times 10^6 \pm 11000$ | 20% | Stimulation |

TABLE 9

In vitro experiment 3. Experimental design to determine the effect of 3 treatments on the DNA content, numbers of viable P388 leukemia cells and the amount of $^3$H—(N)— mevalonate[1] incorporated into cholesterol incubated at 37° C. for 48 hours.

| Treatments | ml Treatment Added | ml P388 cells Added ($10^6$ cells/ml) | RPMI Media |
|---|---|---|---|
| PBS Control[2] | 2 ml | 20 ml | 40 ml & 10% FBS |
| IMIC[3] | 2 ml | 20 ml | 40 ml & 10% FBS |
| Extraction and Isolation Control[4] | 2 ml | 20 ml | 40 ml & 10% FBS |

[1]Prepared as follows: 40 ul of 4 uCi $^3$H—(N)— mevalonate was added to each treatment. After incubation at 37° C. for 48 hours, 10 mls of cell culture was removed and centrifuged at 1760 rpm for 10 minutes. The pellet and supernate were placed in separate incubation flasks. Two mls of PBS was added to rinse each of the centrifuge tubes to remove any of the remaining tracing.
[2]Prepared as follows: Two mls of sterile PBS was added as treatment.
[3]Prepared as follows: 4 grams of FDB was added to 280 ml/80 ml/40 ml (MeOH/HCOOH/H$_2$O) following the procedures in Example 1. The IRF was reconstituted with (10 mls/gram FDB) PBS. Treatment was adjusted to pH 7.4 and filtered through a .45μ and .2μ filtering flask.
[4]Prepared as follows: Prepared wame as #3 except water was substituted for FDB.

TABLE 9a

In Vitro experiment 3. Effect of 3 treatments on (a) the DNA content and the numbers of viable P388 leukemia cells and (b) the amount of $^3$H-mevalonate incorporated into cholesterol incubated at 37° C. for 48 hours.

| (a) Treatment | Numbers of Viable P388 cells/ml | % Inhibition C/D | DNA Content ug/ml | % Inhibition C/D |
|---|---|---|---|---|
| Control | $1.05 \times 10^6 \pm 1800$ | — | 335 | — |
| Extraction and Isolation Blank | $1.40 \times 10^6 \pm 12000$ | — | 300 | — |

TABLE 9a-continued

In Vitro experiment 3. Effect of 3 treatments on (a) the DNA content and the numbers of viable P388 leukemia cells and (b) the amount of $^3$H-mevalonate incorporated into cholesterol incubated at 37° C. for 48 hours.

| | | | | |
|---|---|---|---|---|
| IMIC | .51 × 10$^6$ ± 2100 | 54%/64% | 209 | 38%/30% |

| (b) Treatment | Average CPM ± SD | % Inhibition C/D |
|---|---|---|
| Control | 3700 ± 1300 | — |
| Extraction and Isolation Blank | 3100 ± 830 | — |
| IMIC | 2000 ± 260 | 47%/37% |

C Calculations Based on PBS Control.
D Calculations Based on Extraction Blank.

TABLE 10

In vivo experiment 1. Experimental design to determine the effect of feeding proteose-epetone fraction on P388 leukemia cell numbers and DNA content following IP injection of 10$^6$ viable P388 cells/.6 ml into 26-day-old DBA/2, male mice.

| Treatment | Proteose-peptone Acclimation Time | # Days after P388 Injections | | |
|---|---|---|---|---|
| | | Group 1 | Group 2 | Group 3 |
| Control[1] | 14 Days | 7 Days | 14 Days | 21 Days |
| IMIC[2] | 14 Days | 7 Days | 14 Days | 21 Days |

[1]Control group consisted of 12 mice. Control animals received fresh water and mouse chow ad libitum.
[2]IMIC group consisted of 12 mice. Treatment mice were supplied with crude proteose-peptone fraction in their water bottles, ad libitum. Fresh proteose-peptone was supplied daily.

TABLE 10a

In vivo experiment 1. Effect of feeding proteose-peptone fraction on viable P388 leukemia cell numbers and DNA content following IP injection of 10$^6$ viable P388 cells/.6 ml in 26-day-old DBA/2, male mice.

| Treatment | Numbers of Viable P388 cells/ml | | | DNA Content (ug/ml) | | |
|---|---|---|---|---|---|---|
| | A | B | C | A | B | C |
| Control | 3.78 × 10$^7$ ± 5700 | 1.49 × 10$^7$ ± 16000 | .36 × 10$^7$ ± 3500 | 510 | 125 | 110 |
| Proteose-peptone fed | 2.25 × 10$^7$ ± 4400 | .48 × 10$^7$ ± 44000 | .17 × 10$^7$ ± 12000 | 177 | 62 | 42 |
| % Inhibition based on control | 41% | 68% | 53% | 65% | 50% | 62% |

A 1 week after P388 injection.
B 2 weeks after P388 injection.
C 3 weeks after P388 injection.

TABLE 11

In vivo experiment 2. Experimental design to determine the effect of feeding proteose-peptone fraction on P388 leukemia cell numbers following IP injection of 10$^6$ viable P388 cells/.6 ml into 26-day-old B$_6$D$_2$F$_1$/J, male mice.

| Treatment | Proteose-peptone Acclimation Time | # Days After P388 Injection |
|---|---|---|
| Control[1] | 9 Days | 7 Days |
| IMIC[2] | 9 Days | 7 Days |

[1]Control group consisted of 11 mice. Control animals recieved fresh water and mouse chow ad libitum.
[2] IMIC group consisted of 8 mice. Treatment mice were supplied with crude proteose-peptone fraction in their water bottles, ad libitum. Fresh proteose-peptone was supplied daily.

TABLE 11a

In vivo experiment 2. Effect of feeding proteose-peptone fraction on the viable P388 leukemia cell numbers following IP injection of 10$^6$ viable P388 cells/.6 ml in 26-day-old B$_6$D$_2$F$_1$/J. male mice

| Treatment | Numbers of Viable P388 Cells 1 Week After IP Injection |
|---|---|
| Control | 2.92 × 10$^7$ ± 2600 |
| Proteose-peptone Fed Mice | 1.19 × 10$^7$ ± 6800 |
| % Inhibition Based on Control | 59% |

TABLE 12

In vivo experiment 3. Experimental design to determine the effect of daily[1] IP injections of various treatments on the numbers of P388 leukemia cells surviving after IP injection 24 hours prior to treatments in male DBA/2, 26-day-old mice.

| Treatment | # Mice per Treatment | # P388 Cells Injected | Duration of Treatments |
|---|---|---|---|
| IMIC[2] | 12 | 10$^6$ Cells/.1 ml | 6 Days |
| Control[3] | 14 | 10$^6$ Cells/.1 ml | 6 Days |
| Orotic Acid and IMIC[4] | 12 | 10$^6$ Cells/.1 ml | 6 Days |

[1]Procedure as follows: Mice recieved daily IP injections (.6 ml) for 6 days. The treatments started 24 hours after the IP injection of 10$^6$ viable P388 cells/.1 ml.
[2]Prepared as follows: 4 grams of FDB was added to 280 ml/80 ml/40 ml (MeOH/H-COOH/H$_2$O) following the procedures in Example 1. The IRF was reconstituted with (10 ml/gram FDB) Ringers Locke. Treatment was adjusted to pH 7.4 and filtered through a .2μ and .45μ tissue culture filter.
[3]Control recieved daily IP injections of .6 ml Ringers Locke solution.
[4]Prepared as follows: 15 ml of orotic acid was prepared by autoclaving 25 mg orotic acid in 100 ml Ringers Locke, then adding 15 ml of this to the dry IMIC prepared in FIG. 7. Treatment was adjusted to pH 7.4 and filtered through a .45μ and .2μ tissue culture filter.

TABLE 12a

In vivo experiment 3. Effect of daily injections (IP) of various treatments on the numbers of viable P388 leukemia cells after IP injection 24 hours prior to treatments in 26-day-old DBA/2, male mice.

| Treatment | Numbers of Viable P388 cells/ml | | | % Inhibition | | |
|---|---|---|---|---|---|---|
| | A | B | C | A | B | C |
| Control | $1.65 \times 10^6 \pm$ 73000 | $9.88 \times 10^6 \pm$ 11000 | $1.01 \times 10^6 \pm$ 350 | — | — | — |
| IMIC | $.30 \times 10^6 \pm$ 100000 | $.47 \times 10^6 \pm$ 41000 | $.07 \times 10^6 \pm$ 3500 | 82% | 95% | 93% |
| Orotic acid and IMIC | $3.80 \times 10^6 \pm$ 510000 | $3.45 \times 10^6 \pm$ 34000 | $.57 \times 10^6 \pm$ 1400 | Stimulation | 65% | 43% |

A 1 week after P388 injection.
B 10 days after P388 injection.
C 63 days after P388 injection.

TABLE 13

In vivo experiment 4. Experimental design to determine the effect of daily[1] IP injections of various treatments on DNA content and numbers of viable P388 leukemia cells surviving after IP injection 24 hours prior to treatments in male DBA/2, 26-day-old mice.

| Treatment | # Mice per Treatment | # P388 Cells Injected | Duration of Treatments |
|---|---|---|---|
| IMIC[2] | 6 | $10^6$ Cells/.6 ml | 6 Days |
| Orotic Acid and IMIC[3] | 6 | $10^6$ Cells/.6 ml | 6 Days |
| Orotic Acid[4] | 6 | $10^6$ Cells/.6 ml | 6 Days |
| Control[5] | 11 | $10^6$ Cells/.6 ml | 6 Days |

[1]Procedure as follows: Mice recieved daily IP injections (.6 ml) for 6 days. The treatments started 24 hours after the IP injection of $10^6$ viable P388 cells/.6 ml.
[2]Prepared as follows: 4 grams of FDB was added to 280 ml/80 ml/40 ml (MeOH/H-COOH/H$_2$O) following the procedures in Example 1. The IRF was reconstituted with (10 ml/gram FDB) PBS. Treatment was adjusted to pH 7.4 and filtered through a .45$\mu$ and .2$\mu$ tissue culture filter.
[3]Prepared as follows: 4 grams of FDB was added to 280 ml/80 ml/40 ml (MeOH/H-COOH/H$_2$O) following the procedures in Example 1. The IRF was reconstituted with 40 ml of orotic acid prepared in #4. Treatment was adjusted to pH 7.4 and filtered through a .45$\mu$ and .2$\mu$ tissue culture filter.
[4]Prepared as follows: 25 mg of orotic acid was added to 100 ml PBS and autoclaved at 121° C., 18 PSIG for 15 minutes. Treatment was adjusted to pH 7.4 and filtered through a .45$\mu$ and .2$\mu$ tissue culture filter.
[5]Control recieved daily IP injections of .6 ml PBS for 6 days, following an IP injection of $10^6$ P388 cells/.6 ml.

TABLE 14

In vivo experiment 5. Experimental design to determine the effect of daily[1] IP injections of various treatments on the numbers of P388 leukemia cells surviving after IP injection 24 hours prior to treatments in male $B_6D_2F_1/J$, 26-day-old mice.

| Treatment | # Mice per Treatment | # P388 Cells Injected | Duration of Treatments |
|---|---|---|---|
| IMIC-A[2] | 6 | $10^6$ Cells/.6 ml | 6 Days |
| IMIC-B[3] | 6 | $10^6$ Cells/.6 ml | 6 Days |
| Extraction and Isolation Blank[4] | 6 | $10^6$ Cells/.6 ml | 6 Days |
| Control[5] | 6 | $10^6$ Cells/.6 ml | 6 Days |

[1]Procedure as follows: Mice recieved daily IP injections (.6 ml) for 6 days. The treatments started 24 hours after the IP injection of $10^6$ viable P388 cells/.6 ml.
[2]Prepared as follows: 4 grams of FDB was added to 280 ml/80 ml/40 ml (MeOH/H-COOH/H$_2$O) following the procedures in Example 1. The IRF was reconstituted with (10 ml/gram FDB) PBS. Treatment was adjusted to pH 7.4 and filtered through a .45$\mu$ and .2$\mu$ tissue culture filter.
[3]Prepared as follows: Similar to 2, except no column treatment. The IWBF was adjusted to pH 7.4 40 ml of orotic acid prepared in #4. Treatment was adjusted to pH 7.4 and filtered through a .45$\mu$ and .2$\mu$ tissue culture filter.
[4]Prepared as follows: Same as procedure #2, except distilled water was substituted for FDB.
[5]Control recieved daily injections of sterile PBS for 6 days, 24 hours after the P388 injection.

TABLE 13a

In vivo experiment 4. Effect of daily IP injections of various treatments on the DNA content and numbers of viable P388 leukemia cells after injection 24 hours prior to treatments in 26-day-old DBA/2, male mice.

| Treatment | Numbers of Viable P388 cells/ml | % Inhibition | DNA Content ug/ml | % Inhibition |
|---|---|---|---|---|
| Control | $6.75 \times 10^7 \pm 700000$ | — | 439 | — |
| Orotic Acid | $4.20 \times 10^7 \pm 630000$ | 38% | 428 | — |
| IMIC | $4.19 \times 10^7 \pm 440000$ | 38% | 396 | 10% |
| Orotic Acid and IMIC | $5.48 \times 10^7 \pm 220000$ | 19% | 358 | 12% |

TABLE 14a

In vivo experiment 5. Effect of daily IP injections of various treatments on the numbers of viable P388 leukemia cells after IP injection, 24 hours prior to treatments in 26-day-old $B_6D_2F_1/J$, male mice.

| Treatment | Numbers of Viable P388 Cells/ml | % Inhibition Based on PBS Control | % Inhibition Based on Extraction Control |
|---|---|---|---|
| PBS Control | $8.43 \times 10^7 \pm 440000$ | — | — |
| Extraction and Isolation Control Blank | $6.52 \times 10^7 \pm 710000$ | 22% | — |
| IMIC | $5.73 \times 10^7 \pm 420000$ | 31% | 12% |
| IMIC Filter Only (No column treatment) | $5.16 \times 10^7 \pm 270000$ | 37% | 20% |

TABLE 15

In vivo experiment 5. Experimental design to determine the effects of daily[1] IP injections of various treatments on the DNA content and numbers of P388 leukemia cells surviving after IP injection of 24 hours prior to treatment in male $B_6D_2F_1/J$, 26-day-old mice.

| Treatment | # Mice per Treatment | Duration of Treatment |
| --- | --- | --- |
| IMIC[2] | 6 | 6 Days |
| Extraction and Isolation Blank[3] | 6 | 6 Days |
| Control[4] | 6 | 6 Days |

[1]Procedure as follows: Mice recieved daily IP injections (.6 ml) for 6 days. The treatments started 24 hours after the IP injection of $10^6$ viable P388 cells/.6 ml.
[2]Prepared as follows: 4 gram of FDB was added to 280 ml/80 ml/40 ml (MeOH/H-COOH/H$_2$O) following the procedures in Example 1. The IRF was reconstituted with (10 ml/ gm FDB) PBS. Treatment was adjusted to pH 7.4 and filtered through a .45μ and .2μ filtering flask.
[3]Prepared as follows: Same as #2, except distilled water was substituted for FDB.
[4]Control recieved daily injections of sterile PBS ofr 6 days, 24 hours after the P388 IP injection.

TABLE 15a

In vivo experiment 6. Effect of daily IP injections of various treatments on DNA content and numbers of viable P388 leukemia cells after IP injection 24 hours prior to treatments in 26-day-old $B_6D_2F_1/J$ male mice.

| Treatment | Numbers of Viable P388 cells/ml | % Inhibition Based on PBS Control | % Inhibition Based on Extraction Blank | DNA Content ug/ml | DNA Content % Inhibition A/B |
| --- | --- | --- | --- | --- | --- |
| Control | $1.65 \times 10^6 \pm 30000$ | — | — | 159 | — |
| Extraction and Isolation Control Blank | $1.66 \times 10^6 \pm 42000$ | — | — | 142 | — |
| IMIC | $1.33 \times 10^6 \pm 29000$ | 19% | 20% | 120 | 24%/15% |

A Based on PBS Control
B Based on Extraction Control

What is claimed:

1. An antineoplastic agent designated IMIC having the following characteristics:
   (a) present in the retentate of dialyzed skim milk;
   (b) has a molecular weight of about 165–230;
   (c) bound to a protein in the proteose-peptone fraction of milk;
   (d) non-dialyzable in the native state;
   (e) soluble in water;
   (f) insoluble in organic hydrocarbon solvents;
   (g) acid stable;
   (h) not bound or retained by a $C_{18}$ or $C_8$ reverse phase HPLC columns.
   (i) not retained by a $C_{18}$ or silica gel sep. pak;
   (j) has λ maximum absorbance at 207 nm and 278 nm (UV) in neutral and acidic solution and in a basic solution at 223 and 290 nm;
   (k) provides a bioactive peak with a retention time of about 7.0 to about 7.8 minutes upon fractionation by HPLC (High Performance Liquid Chromatography) on a Biorad Aminex 87 WX resin column (30 cm × 7.9 mm) with 0.05 NH$_3$SO$_4$ as the mobile phase and with a flow rate of 0.7 ml/minute;
   (l) provides a bioactive peak with a retention time of about 9.9 minutes upon fractionation on an HPLC Biorad Ag 50 WX-8 resin column (22 mm × 30 cm) with 0.035N formic acid as the mobile phase and a flow rate of 4 ml/minutes.
   (m) inhibits cholesterolgenesis.

2. A process for producing an antineoplastic agent, IMIC, comprising:
   (a) heating whey at a temperature and for a time sufficient to precipitate whey proteins;
   (b) removing precipitated whey proteins and retaining a supernatant;
   (c) filtering the supernatant and obtaining a retentate; and
   (d) recovering IMIC from the retentate;

3. The process of claim 2 wherein IMIC is recovered by:
   (e) reconstituting the retentate; and
   (f) repeating steps (c) and (e) a sufficient number of times to provide a condensed retentate substantially free of proteins except proteose-peptone.

4. The condensed retentate prepared by the process according to claim 2.

5. A process according to claim 3 wherein the condensed retentate is freeze-dried.

6. The process according to claim 5 wherein IMIC is further pruified by separating proteose-peptone fom IMIC in a solvent.

7. The process according to claim 6 wherein the separation is achieved by:
   (a) mixing the freeze-dried retentate in a methanol:-formic acid:water solvent;
   (b) sonicating, refrigerating and centrifuging the mixture of step (a) and retaining a supernatant;
   (c) evaporating the supernatant for dryness;
   (d) reconstituting the supernatant.

8. The process according to claim 7 which comprises:
   (e) repeating steps (c) and (d) a sufficient number of times to remove any remaining solvent;
   (f) eluting IMIC from the supernatant by column chromatography.

9. The condensed retentate prepared by the process according to claim 5.

10. A product produced by the method of claim 2.

11. A product produced by the method of claim 3.

12. A product produced by the method of claim 7.

13. A product produced by the method of claim 8.

14. An antineoplastic composition comprising an antineoplastic effective amount of IMIC as defined in claim 1 and pharmaecutically acceptable carrier.

15. The composition of claim 14 having a unit dosage form containing from about 150 to about 400 mg. of IMIC.

16. A method of treating neoplastic diseases comprising the administration of an effective amount of an antineoplastic agent designated IMIC having the following characteristics:
   (a) present in the retentate of dialyzed skim milk;
   (b) has a molecular weidht of about 165–230;
   (c) bound to a protein in the proteose-peptone fraction of milk;
   (d) non-dialyzable in the native state;

(e) soluble in water
(f) insoluble in organic hydrocarbon solvents;
(g) acid stable;
(h) not bound or retained by a $C_{18}$ or $C_8$ reverse phase HPLC columns.
(i) not retained by a $C_{18}$ or silica gel sep. pak;
(j) has λ maximum absorbance at 207 nm and 278 nm (UV) in neutral and acidic solution and in a basic solution at 223 and 290 nm;
(k) provides a bioactive peak with a retention time of about 7.0 to about 7.8 minutes upon fractionation by HPLC (High Performance Liquid Chromatography) on a Biorad Aminex 87 WX resin column (30 cm ×7.9 mm) with 0.05 $NH_2SO_4$ as the mobile phase and with a flow rate of 0.7 ml/minute;
(l) provides a bioactive peak with a retention time of about 9.9 minutes upon fractionation on an HPLC Biorad Ag 50 Wx-8 resin column (22 mm×30 cm) with 0.035N formic acid as the mobil phase and a flow rate of about 4 ml/minutes.
(m) inhibits cholesterolgenesis.

17. The method of claim 16 wherein said IMIC is administered in an amount from about 2 to about 4 mg/kg of body weight per day.

* * * * *

UNITED STATES PATENT AND TRADEMARK OFFICE
CERTIFICATE OF CORRECTION

PATENT NO. : 5,019,390

DATED : May 28, 1991

INVENTOR(S) : Robert D. McCarthy, et al.

It is certified that error appears in the above-identified patent and that said Letters Patent is hereby corrected as shown below:

In the Abstract, line 8: "fration" should read as --fraction--

In the Abstract, line 16: "208" should read as --207--

In the Abstract, line 21: "7.9 nm" should read as --7.9 mm--

In the Abstract, line 25: "Mx-8" should read as --Wx-8--

Column 3, line 10: delete second occurrence of "pak;"

Column 3, line 31: "he" should read as --the--

Column 3, line 67: "mobile" should read as --mobil--

Column 6, line 46: "rangeing" should read as --ranging--

Column 7, lines 4-5: after "preparations" insert --should contain at least 1% of active compound. The--

UNITED STATES PATENT AND TRADEMARK OFFICE
CERTIFICATE OF CORRECTION

PATENT NO. : 5,019,390

DATED : May 28, 1991

INVENTOR(S) : Robert D. McCarthy, et al.

It is certified that error appears in the above-identified patent and that said Letters Patent is hereby corrected as shown below:

Column 9, line 10: "13The" should read as --13. The--

Column 9, line 63: "resohicated" should read as --resonicated--

Column 9, line 68: "rename" should read as --remove--

Column 17, line 40, Table 3: "85%" should read as --86%--

Column 17, line 62, Table 5: "pyrophophate" should read as --pyrophosphate--

Column 18, line 4, Table 5: "pyrophophate" should read as --pyrophosphate--

Column 18, line 62, Table 7: "onthe" should read as --on the--

Column 20, line 19: ".45μ tissue" should read as --.45μ and .2μ tissue--

Column 20, line 29, Table 8: "Garry" should read as --Carry--

Column 20, line 51, Table 9: "40 μl of 4" should read as --50 μl of 5--

UNITED STATES PATENT AND TRADEMARK OFFICE
CERTIFICATE OF CORRECTION

PATENT NO. : 5,019,390
DATED : May 28, 1991
INVENTOR(S) : Robert D. McCarthy, et al.

It is certified that error appears in the above-identified patent and that said Letters Patent is hereby corrected as shown below:

Column 20, line 58, Table 9: "wame" should read as --same--

Column 21, line 19, Table 10: "epetone" should read as --peptone--

Column 24, lines 35-36: delete "40 ml of orotic acid prepared in #4. Treatment was adjusted to pH 7.4"

Column 25, line 62, Claim 1: "mobile" should read as --mobil--

Column 26, line 9, Claim 3: "repreating" should read as --repeating--

Column 26, line 17, claim 6: "pruified" should read as --purified--

Column 17, Table 2, 85% should read -- 86% --.

Signed and Sealed this

Ninth Day of November, 1993

BRUCE LEHMAN

*Attest:*

*Attesting Officer*  *Commissioner of Patents and Trademarks*